(12) United States Patent
Bialer et al.

(10) Patent No.: US 6,969,732 B2
(45) Date of Patent: Nov. 29, 2005

(54) PROPYLISOPROPYL ACETIC ACID AND PROPYLISOPROPYL ACETAMIDE STEREOISOMERS, A METHOD FOR THEIR SYNTHESIS AND PHARMACEUTICAL COMPOSITIONS CONTAINING THEM

(75) Inventors: Meir Bialer, Jerusalem (IL); Ofer Spigelstein, Mevasseret Zion (IL); Boris Yagen, Jerusalem (IL)

(73) Assignee: Yissum Research Development Company of the Hebrew University of Jerusalem, Jerusalem (IL)

( * ) Notice: Subject to any disclaimer, the term of this patent is extended or adjusted under 35 U.S.C. 154(b) by 0 days.

(21) Appl. No.: 10/420,560

(22) Filed: Apr. 22, 2003

(65) Prior Publication Data
US 2003/0212131 A1 Nov. 13, 2003

Related U.S. Application Data

(63) Continuation of application No. 09/673,296, filed as application No. PCT/IL99/00197 on Apr. 12, 1999, now Pat. No. 6,630,602.

(51) Int. Cl.[7] .................... A61K 31/16; C07C 233/00
(52) U.S. Cl. ........................... 514/625; 564/215
(58) Field of Search ......................... 514/625, 557, 514/563; 564/215, 143; 562/512

(56) References Cited

U.S. PATENT DOCUMENTS

| | | |
|---|---|---|
| 3,145,877 A * | 8/1964 | Adams et al. |
| 4,988,731 A * | 1/1991 | Meade |
| 5,786,380 A | 7/1998 | Nau et al. |
| 6,201,021 B1 | 3/2001 | Ohuchida et al. |

FOREIGN PATENT DOCUMENTS

| WO | WO 9830536 | 7/1998 |
|---|---|---|

OTHER PUBLICATIONS

Abdata, Eschborn, *Pharmazeutische Stoffliste 10, Auflage, Valpromid.*

Bojic et al, *Further Branching of Valproate–Related Carboxylic Acids Reduces the Teratogenic Activity, but Not the Anticonvulsant Effect*, Chemical Research in Toxicology, vol. 9, pp. 866–870 (1986).

Canin Koch et al, *Enantioselective Preparation of beta–Alkyl–gamma–butyrolactones from Functionalized Ketene Dithioacetals*, Journal of Organic Chemistry, vol. 58, pp. 2725–2737 (1983).

Stang et al, *Perfluoroalkanesulfonic Esters: Methods of Preparation and Applications in Organic Chemistry*, Synthesis, pp. 85–126 (1982).

Barel, Shimon et al., "Stereoselective pharmacokinetic analysis of valnoctamide in healthy subjects and in patients with epilepsy" *Clinical Pharmacology & Therapeutics* (Apr. 1997) pp. 442–449.

Bialer, Meir et al., Can we develop improved derivatives of valproic acid? *Pharmacy World & Science*, vol. 16, No. 1 (1994) pp. 2–6.

Haj–Yehia, Abdulla et al., "Structure–pharmacokinetic relationships in a series of short fatty acid amides that possess anticonvulsant activity" *Journal of Pharmaceutical Sciences*, vol. 79, No. 8 (Aug. 1990) pp. 719–724.

Haj–Yehia, Abdulla et al., "Structure–pharmacokinetic relationships in a series of short fatty acid amides that possess anticonvulsant activity" *Chemical Abstracts* 113:204430b (1990).

Haj–Yehia, Abdulla et al., "Structure–pharmacokinetic relationships in a series of valpromide derivatives with antiepileptic activity" *Pharmaceutical Research*, Vo. 6, No. 8 (1989) pp. 683–689.

Haj–Yehia, Abdulla et al., "Structure–pharmacokinetic relationships in a series of valpromide derivatives with antiepileptic activity" *Pharmacology Abstracts* 111:186922r (1989).

(Continued)

*Primary Examiner*—Paul A. Zucker
(74) *Attorney, Agent, or Firm*—Mayer, Brown, Rowe & Maw LLP; David B. Fournier

(57) ABSTRACT

The present invention relates to racemic propylisopropyl acetic acid and propylisopropyl acetamide and their isomers in their racemic and stereospecific forms, for use in treatment of neurological and psychotic disorders, and affective disorders and to treat pain, headaches and migraines. The isomers are of the compound formula I

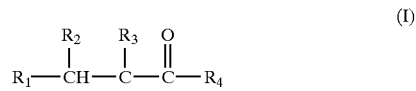

$R_1$ is a methyl or ethyl group;
$R_2$ is H, methyl or an ethyl group;
$R_3$ is ethyl or a propyl group; and
$R_4$ is a hydroxyl or amide group, and the total number of carbon atoms in said compound is 8, provided that when R1 is a methyl group and R4 is an amide group, R2 and R3 are not ethyl, further provided that when R1 is an ethyl and R4 a hydroxyl group, only stereoisomers of the compound are referred to.

The present invention further relates to a method for the stereoselective synthesis of the 2R stereoisomer of PID and PIA. The present invention also relates to pharmaceutical compositions containing as an active ingredient a racemic mixture or stereoisomers of the compounds of the general formula (I), which are useful for the treatment of neurological and psychotic disorders, and affective disorders and to treat pain, headaches and migraines.

8 Claims, 6 Drawing Sheets

OTHER PUBLICATIONS

Isoherranen, Nina et al., "Characterization of the anticonvulsant profile and enantioselective pharmacokinetics of the chiral valproylamide propylisopropyl acetamide in rodents" *British Journal of Pharmacology*, vol. 138, No. 4 (2003) pp. 602–613.

Loscher, W. et al., "Pharmacological evaluation of various metabolites and analogues of valproic acid" Neuropharmacology, vol. 24, No. 5 (1985) pp. 427–435.

Spiegelstein, Ofer et al., Stereoselective pharmacokinetics and pharmacodynamics of propylisopropyl acetamide, a CNS–active chiral amide analog of valproic acid Pharmaceutical Research, vol. 16, No. 10 (1999) pp. 1582–1588.

*The Merck Index Encyclopedia of Chemicals, Drugs and Biologicals*, Twelfth Edition (1996) Pentanoic acid on the name index page; valproic acid and valpromide, p. 1691.

* cited by examiner

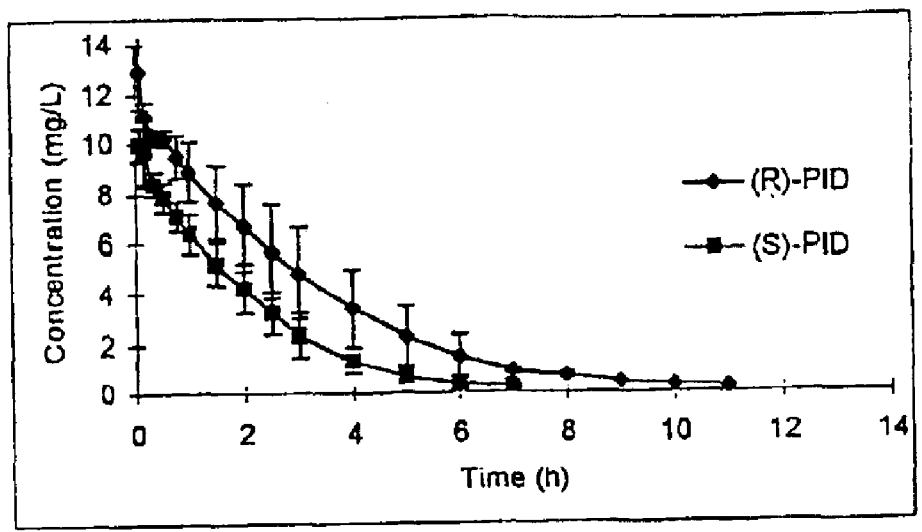
FIGURE 4 : Plasma Concentrations of PID enantiomers after administration of the individual enantiomers.
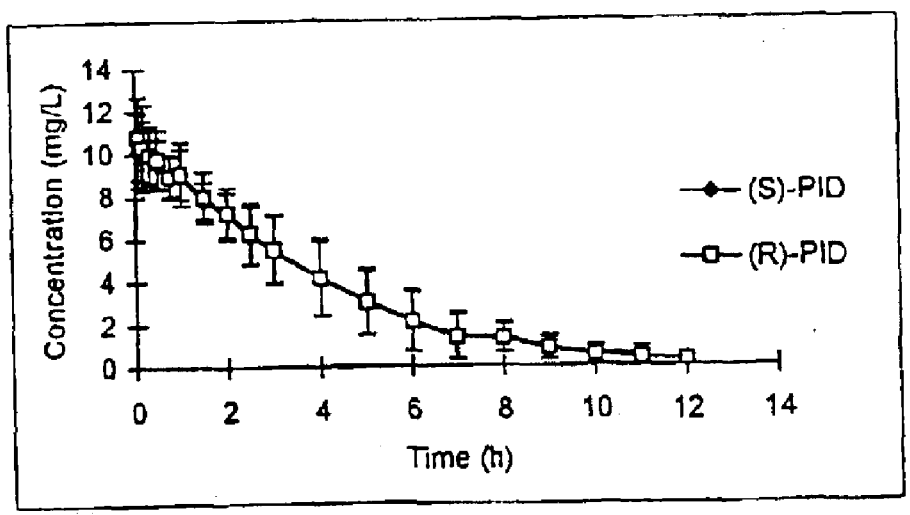
FIGURE 5 : Plasma Concentrations of PID enantiomers after administration of racemic PID.

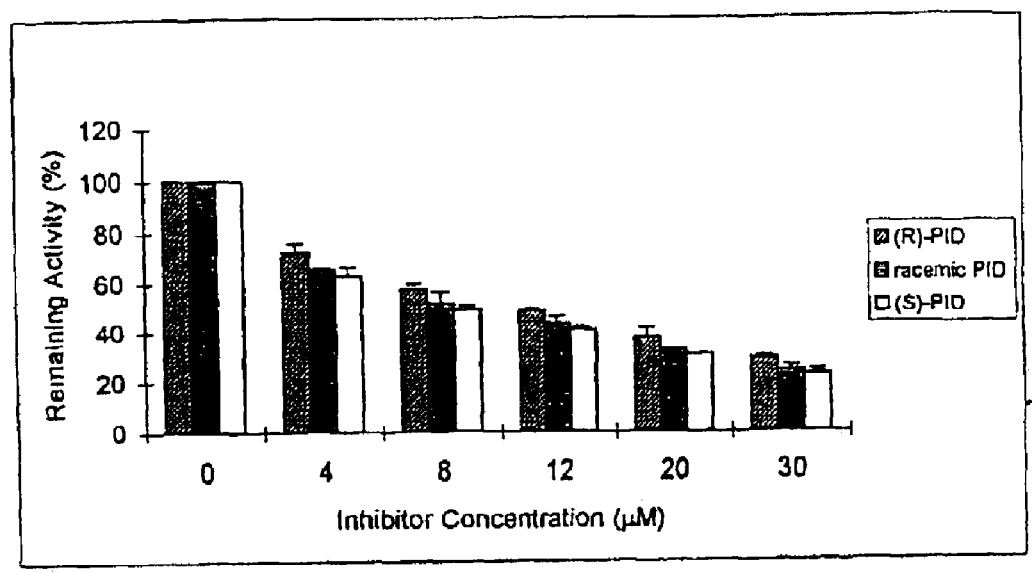
FIGURE 6: Inhibition of Epoxide Hydrolase by PID

METHOD:

RESULTS:

PROPYLISOPROPYL ACETIC ACID AND PROPYLISOPROPYL ACETAMIDE STEREOISOMERS, A METHOD FOR THEIR SYNTHESIS AND PHARMACEUTICAL COMPOSITIONS CONTAINING THEM

This application is a continuation of U.S. patent application Ser. No. 09/673,296 (now U.S. Pat. No. 6,630,602) filed on Nov. 29, 2000 and based on PCT Application Ser. No. PCT/IL99/00197 filed Apr. 12, 1999.

FIELD OF THE INVENTION

The present invention generally relates to propylisopropyl acetic acid (PIA) and propylisopropyl acetamide (PID) in their racemic and stereospecific forms, to some of their isomers and to stereoisomers thereof, for use in treatment of neurological and psychotic disorders, and affective disorders and to treat pain, including headaches and migraine pains. The present invention further relates to a method for the synthesis of PIA and PID stereoisomers. The present invention further relates to pharmaceutical compositions containing, as an active ingredient, said racemic or stereoisomer forms.

BACKGROUND OF THE INVENTION

Headaches, especially in the form of migraine pain are a wide spread malady.

Valproic acid (VPA), also used in antiepileptic therapy, is a drug which was approved for the treatment of migraine and has been utilized in the treatment of epilepsy for the last 25 years with a few side effects. Two major side effects being teratogenicity and hepatotoxicity, have been associated with valproate therapy.

In humans, valpromide (VPD), which is also used as an anticonvulsant agent, is a prodrug of valproic acid (VPA). It was found to be more potent than VPA though it exerted more significant sedative side effects (Loscher W. and Nau H. (1985) Neuropharmacology 24: 427–435).

Isomers of VPD, such as valnoctamide (VCD-valmethamide or 2-ethyl-3-methyl pentanamide), were found to be more potent than valproic acid as anticonvulsants (Haj-Yehia A. and Bialer M. (1989) Pharm Res 6:683–9). Stereoselectivity has been shown in pharmacokinetics in man for an amide of an aliphatic short-chain fatty acid such as valnoctamide (VCD) (Barel S., Yagen B., Schurig V., Soback S., Pisani F., Perucca E. and Bialer M. (1997) Clin. Pharmacol. and Therap. 61 (4): 442–449). This work demonstrated that VCD pharmacokinetics (PK) in humans is stereoselective, with one isomer exhibiting a much higher clearance and a shorter half-life compared with the other three stereoisomers.

The present invention relates to the stereoisomers of PIA and of PID and to their isomers (such as VPD and VCA) for use in treatment of neurological and psychotic disorders, and affective disorders and to treat pain, such as head aches. Although VPA and VPD analogues (such as VCA and VCD) were implicated in the treatment of epilepsy, there is no evidence that they in their racemic form or their individual stereoisomers are active in the treatment of neurological and psychotic disorders, affective disorders and pain.

BRIEF DESCRIPTION OF DRAWINGS

FIG. No. 1 shows the asymmetric synthesis of (R)-propylisopropyl acetamide (R)-PID from starting material of valeroyl chloride and isopropanol through the synthesis of (4S)-benzyl, 3-(1-oxo, (2R)-isopropyl valeroyl) 2-oxazolidinone.

FIG. No. 2 shows the asymmetric synthesis of (R)-propylisopropyl acetamide(R)-PID from (4S)-benzyl, 3-(1oxo, (2R)-isopropyl valeroyl) 2-oxazolidinone.

Figure 1:
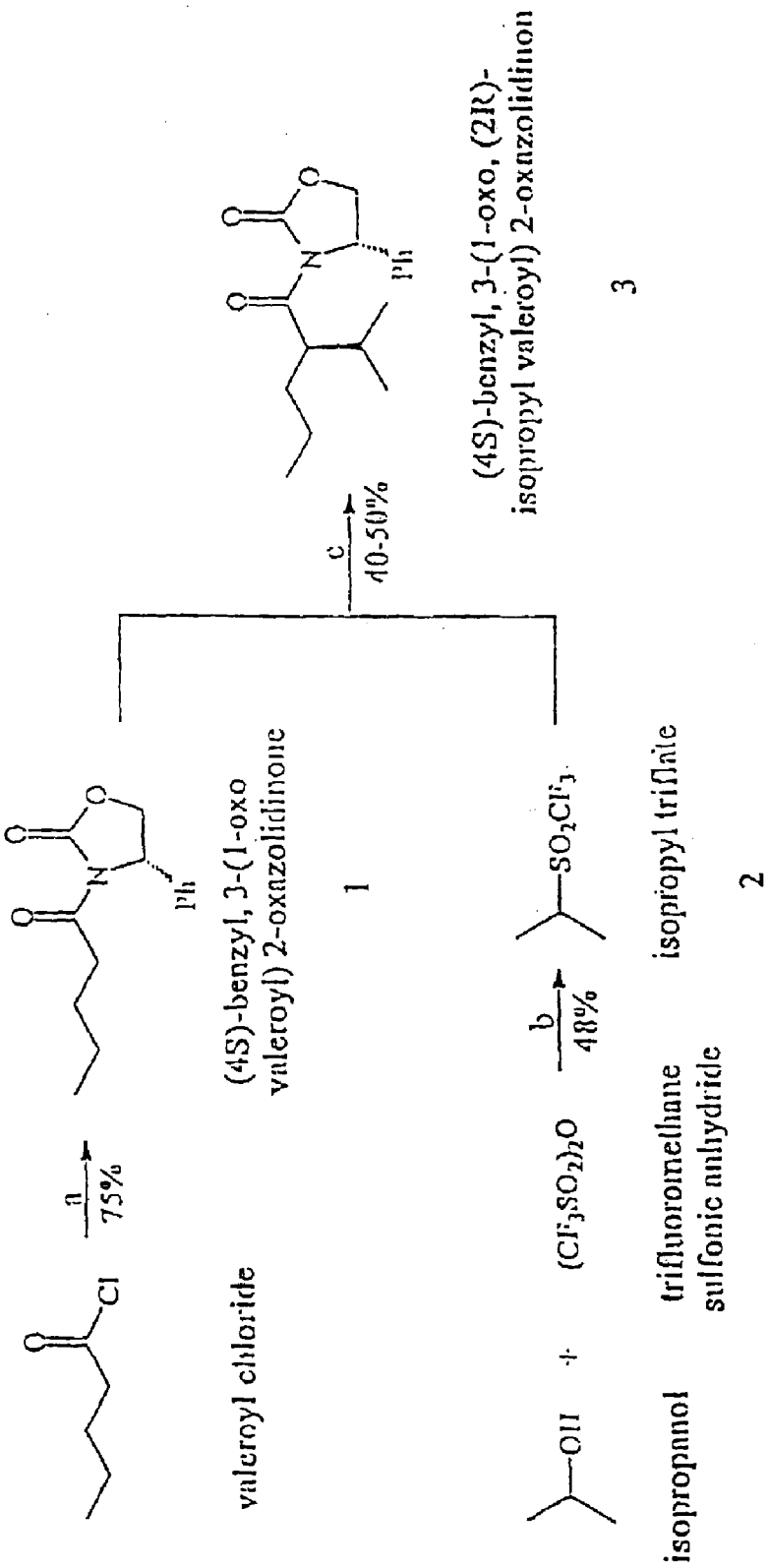

FIG. No. 3 shows the asymmetric synthesis of (S)-propylisopropyl acetamide (S)-PID from (4R)-methyl-(5S)-phenyl-3-(1-oxo valeroyl)-2-oxazolidinone.

FIG. No. 4 shows the average plasma concentrations of the PID enantiomers (R)-PID and (S)-PID for six mongrel dogs over time after administration of the individual enantiomers.

FIG. No. 5 shows the average plasma concentrations of the PID enantiomers (R)-PID and (S)-PID for six mongrel dogs over time after administration of racemic PID.

FIG. No. 6 shows the inhibition of epoxide hydrolase by various concentrations of (R)-PID, (S)-PID and racemic PID.

FIG. No. 7A shows the testing regime used to test the effects of PID on dural plasma protein (bovine serum albumin (BSA)) extravasation evoked by unilateral trigeminal gangelion stimulation in anaesthetized rats.

FIG. No. 7B shows the stimulated/unstimulated versus PID mg/kg effects of PID on dural plasma protein (bovine serum albumin (BSA)) extravasation evoked by unilateral trigeminal gangelion stimulation in anaesthetized rats.

SUMMARY OF THE INVENTION

The present invention relates to racemic propylisopropyl acetic acid and propylisopropyl acetamide and their isomers in their racemic and stereospecific forms, for use in treatment of neurological and psychotic disorders, and affective disorders and to treat pain, headaches and migraines, wherein the isomers are of the compound formula I

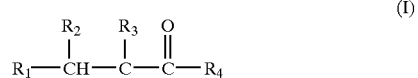

wherein $R_1$ is a methyl or ethyl group;
$R_2$ is H, methyl or an ethyl group;
$R_3$ is ethyl or a propyl group; and
$R_4$ is a hydroxyl or amide group,
wherein the total number of carbon atoms in said compound is 8, provided that when R1 is a methyl group and R4 is an amide group, R2 and R3 are not ethyl, further provided that when R1 is an ethyl and R4 a hydroxyl group, only stereoisomers of the compound are referred to, further provided that when the compounds described by formula I are valpromide ($R_1$=ethyl, $R_2$=H, $R_3$=propyl, $R_4$=NH$_2$), di-isopropylacetic acid ($R_1$=methyl, $R_2$=methyl, $R_3$=isopropyl, $R_4$=OH) and valnoctamide ($R_1$=ethyl, $R_2$=methyl, $R_3$=ethyl, $R_4$=NH$_2$), these compounds are excluded.

The present invention further relates to a method for the stereoselective synthesis of the 2R stereoisomer of PID and PIA comprising;
(a) synthesizing (4S)-3-(1'-oxopentyl)-4-benzyl-2-oxazolidinone from (4S)-benzyl-2-oxazolidinone (or other related oxazolidinone auxiliaries) and valeroyl chloride;
(b) synthesizing of Isopropyl trifluoromethane sulfonate (isopropyl triflate);
(c) synthesizing (4S,2'R)-3-(2'-isopropyl-1'-oxopentyl)-4-benzyl-2-oxazolidinone (d) synthesizing (2R)-propylisopropyl acetic acid ((2R-PIA) and subsequently;

(e) synthesis of (2R)-propylisopropyl acetamide.

and to a method for the stereoselective synthesis of the 2S stereoisomer of PID and PIA comprising;

(a) Synthesizing (4R,5S)-3-(1'-oxopentyl)-4-methyl-5-phenyl-2-oxazolidinone from (4R,5S)-4-methyl-5-phenyl-2-oxazolidinone (or other related oxazolidinone auxiliaries) and valeroyl chloride;

(b) synthesizing (4R,5S,2'S)-3-(2'-isopropyl-1'-oxopentyl)-4-methyl-5-phenyl-2-oxazolidinone;

(c) synthesizing (4S,2'R)-3-(2'-isopropyl-1'-oxopentyl)-4-benzyl-2-oxazolidinone(4S,2'R)-3-(2'-isopropyl-1'-oxopentyl)-4-benzyl-2-oxazolidinone;

(d) synthesizing (2S)-propylisopropyl acetic acid ((2S)-PIA)and subsequently;

(e) synthesis of (2S)-propylisopropyl acetamide.

The present invention also relates to pharmaceutical compositions containing as an active ingredient a racemic mixture or stereoisomers of the compounds of the general formula (I), which are useful for the treatment of neurological and psychotic disorders, and affective disorders and to treat pain, headaches and migraines.

DETAILED DESCRIPTION OF THE INVENTION

The present invention generally relates to propylisopropyl acetic acid (PIA) and propylisopropyl acetamide (PID) in their racemic and stereospecific forms, to some of their isomers and to stereoisomers thereof, for use in treatment of neurological and psychotic disorders, and affective disorders and to treat pain, including head aches and migraine pains. The present invention further relates to the 2S and 2R PIA and PID stereoisomers and to a method for their synthesis. The present invention also relates to pharmaceutical compositions containing, as an active ingredient, these racemic mixtures or stereoisomers.

The present invention relates to PID and PIA or PIA isomers, such as valnoctic acid (VCA) or PID isomers, such as valpromide (VPD) in their racemic or stereospecific forms and to the stereoisomers of chiral valproyl amide analogous of valproic acid (VPA) such as PID, which may be useful in the treatment of neurological and psychotic disorders, and affective disorders and to treat pain.

The present invention relates to pharmaceutical compositions containing, as their active ingredient, PIA or PID isomers of the general formula (I):

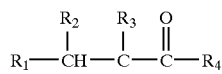

wherein $R_1$ is a methyl or ethyl group;

$R_2$ is H, methyl or an ethyl group;

$R_3$ is ethyl or a propyl group; and $R_4$ is a hydroxyl or amide group, and wherein the total number of carbon atoms is 8. provided that when R1 is a methyl and R4 is an amide group, R2 is not an ethyl and R3 is not an ethyl, further provided that when R1 is an ethyl and R4 a hydroxyl group, only stereoisomers of the compound are referred to, further provided that when the compounds described by formula I are valpromide ($R_1$=ethyl, $R_2$=H, $R_3$=propyl, $R_4$=$NH_2$), di-isopropylacetic acid ($R_1$=methyl, $R_2$=methyl, $R_3$=isopropyl, $R_4$=OH) and valnoctamide ($R_1$=ethyl, $R_2$=methyl, $R_3$=ethyl, $R_4$=$NH_2$), these compounds are excluded.

For example, in PIA R1 is a methyl, R2 is a methyl, R3 is a propyl and R4 is a hydroxyl and in PID R1 is a methyl, R2 is a methyl, R3 is a propyl and R4 is an amide group.

The present invention further relates to a method for the stereoselective synthesis of the propylisopropyl acetic acid and corresponding amide (PIA and PID)) stereoisomers (2R and 2S).

Figure 2:
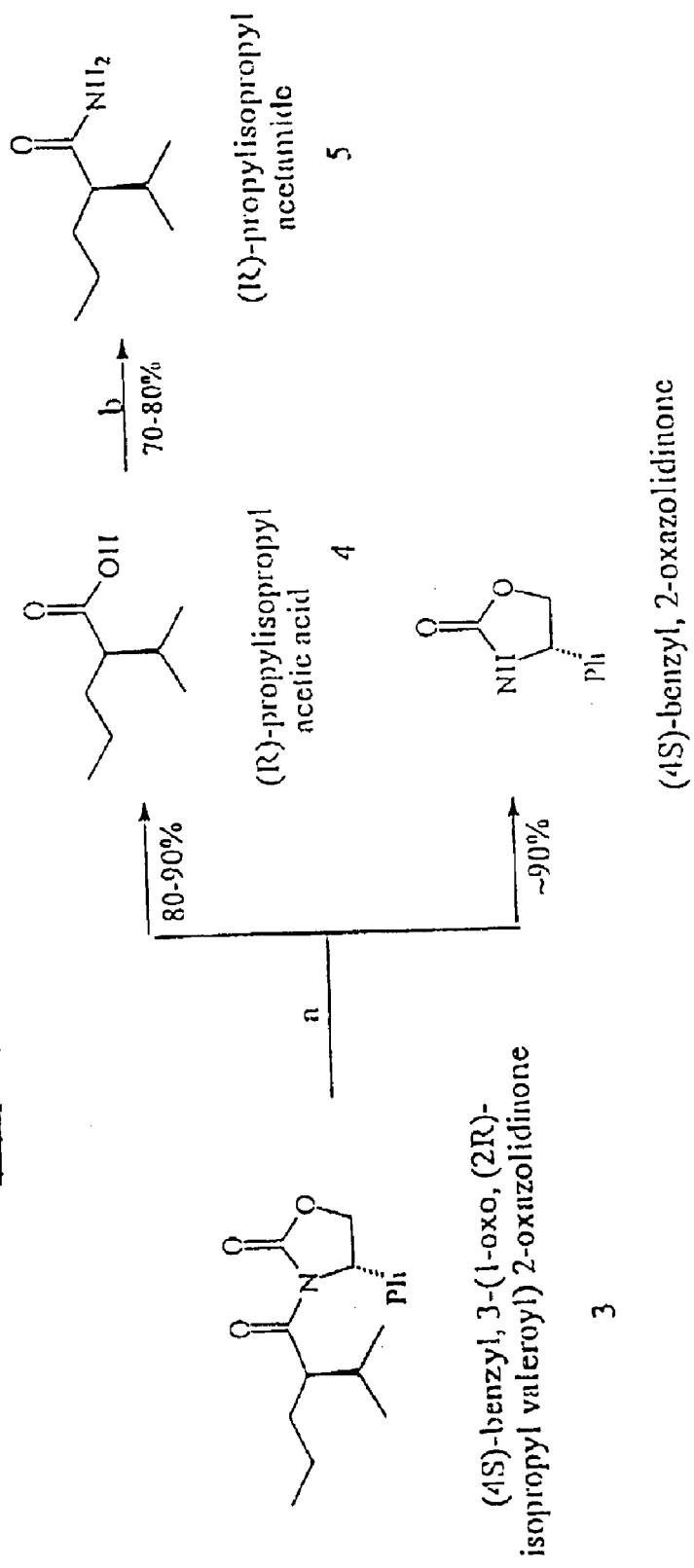

The method of synthesis of the 2R stereoisomers, which is described in FIGS. 1 and 2, comprises the following steps;

(a) synthesizing (4S)-3-(1'-oxopentyl)-4-benzyl-2-oxazolidinone (1) from (4S)-benzyl-2-oxazolidinone (or other related oxazolidinone auxiliaries) and valeroyl chloride;

(b) synthesizing of Isopropyl trifluoromethane sulfonate (isopropyl triflate) (2);

(c) synthesizing (4S,2'R)-3-(2'-isopropyl-1'-oxopentyl)-4-benzyl-2-oxazolidinone(4S,2'R)-3-(2'-isopropyl-1'-oxopentyl)-4-benzyl-2-oxazolidinone (3);

(d) synthesizing (2R)-propylisopropyl acetic acid (2R-PIA) (4) and subsequently;

(e) synthesis of (2R)-propylisopropyl acetamide (5).

Figure 3:
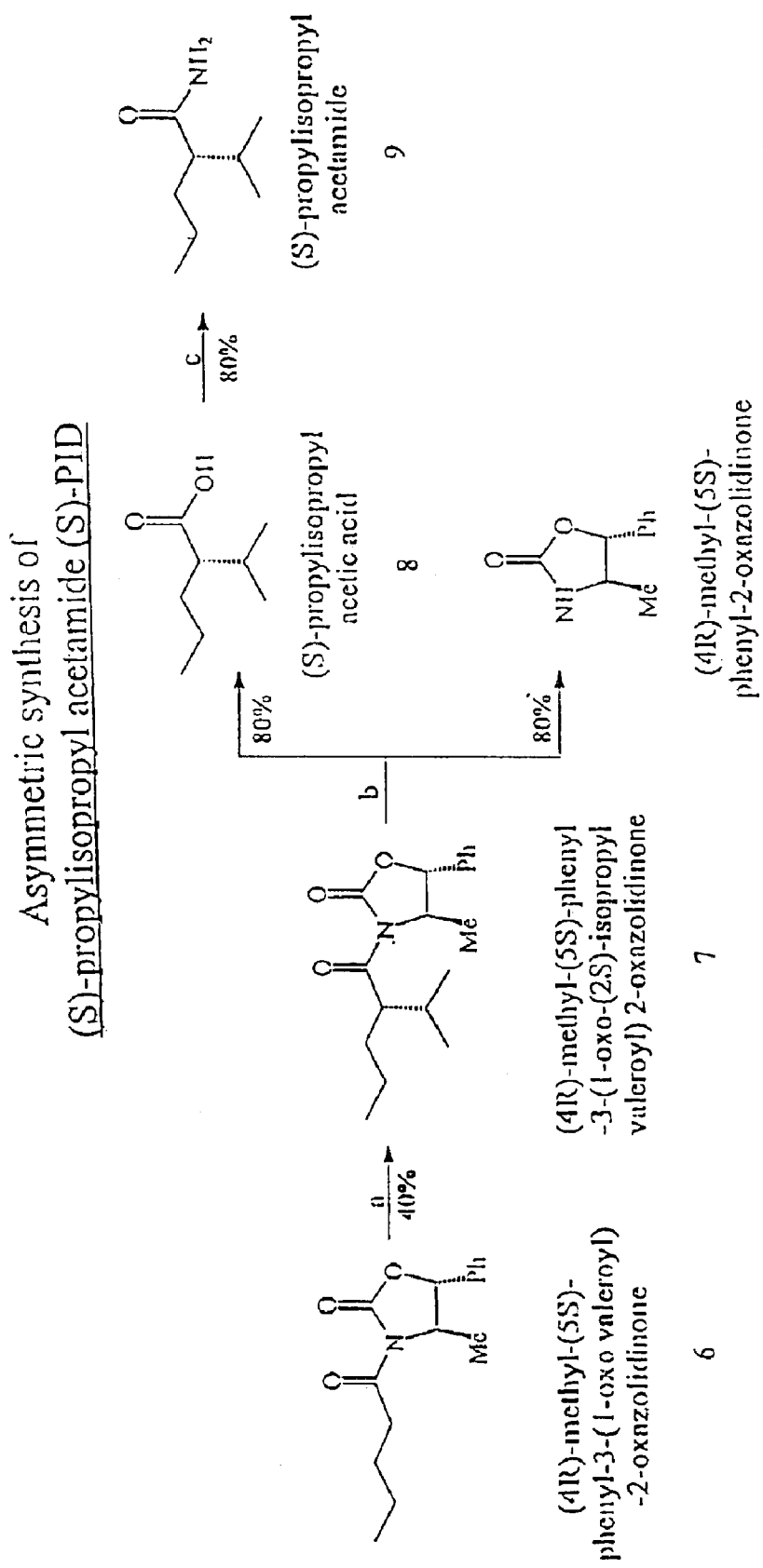

The method of synthesis of the 2S stereoisomers, which is described in FIG. 3, comprises the following steps;

(a) Synthesizing (4R,5S)-3-(1'-oxopentyl)-4-methyl-5-phenyl-2-oxazolidinone (6) from (4R,5S)-4-methyl-5-phenyl-2-oxazolidinone (or other related oxazolidinone auxiliaries) and valeroyl chloride;

(b) synthesizing (4R,5S,2'S)-3-(2'-isopropyl-1'-oxopentyl)-4-methyl-5-phenyl-2-oxazolidinone (7);

(c) synthesizing (4S,2'R)-3-(2'-isopropyl-1'-oxopentyl)-4-benzyl-2-oxazolidinone(4S,2'R)-3-(2'-isopropyl-1'-oxopentyl)-4-benzyl-2-oxazolidinone (d) synthesizing (2S)-propylisopropyl acetic acid ((2S)-PIA) (8) and subsequently;

(e) synthesis of (2S)-propylisopropyl acetamide ((2S)-PIA) (9).

The said invention will be further illustrated by the following experiments. These experiments do not intend to limit the scope of the invention, but to demonstrate and clarify it only.

The two enantiomers of PID, (2S)-PID and (2R)-PID, were tested in mice and rats for their antiepileptic (anticonvulsant) activity and for neurotoxicity. Following i.p. administration to mice and oral administration to rats, (2R)-PID was more active and showed better potency than (2S)-PID in the MES and sc Met tests.

In dogs, following iv administration, (2R)-PID had a lower clearance and longer half-life than (2s)-PID, a fact that may contribute to the better anticonvulsant activity of (2R)-PID. The better anticonvulsant activity (compare to VPA) of PID and the lack of its teratogenicity, increases the likelihood that other CNS activities exerted by VPA (treatment of neurological and psychotic disorders, affective disorders pain) is more pronounced by PID in its racemic and stereoisomers forms.

The method for the asymmetric synthesis of the 2R and 2S PID and PIA stereoisomers will be further described by the following examples:

Synthesis of (2R)-propylisopropyl Acetamide 1. (4S)-3-(1'-oxopentyl)4-benzyl-2-oxazolidinone Under $N_2$ to a cooled solution (−78° C.) of (4S)-benzyl-2-oxazolidinone (25 g) in dry THF (150 ml) was added dropwise a solution of n-BuLi (97 ml, 1.6 M in hexane). After stirring the reaction mixture for 30 min, valeroyl chloride (20.1 ml) was added dropwise via cannula, the reaction was slowly warmed to 0° C., at this temperature stirred for 2.5 hours and quenched by saturated NH$_4$CL solution. After evaporation of THF the residue was extracted with dichloromethane (DCM) (3×150 ml). The combined organic extracts washed with water, saturated brine and dried over MgSO$_4$. The product (27.6 g) was crystallized from 10% EtOAc in PE, yield 75%.

2. Isopropyl Trifluoromethane Sulfonate (Isopropyl Triflate)

Under N$_2$ to a cooled (−15° C.) solution of dry isopropanol (10.4 ml) and dry Et$_3$N (25.2 ml) in dry DCM (200 ml) was added dropwise a cooled (−15° C.) solution of Tf$_2$O (triflic anhydride[a]) (49.0 g in 50 ml of DCM). The reaction mixture was stirred for an hour then quenched with cooled (0° C.) HCl solution (0.25 M, 2×350 ml). The organic phase was washed with cooled (0° C.) solution of NaHCO$_3$ (0.5 M, 2×175 ml), dried over MgSO$_4$ and concentrated. The yellowish liquid obtained was dissolved in a cooled (0° C.) pentane solution (50 ml), filtered through a short MgSO$_4$ plug and concentrated. The product (18.3 g) was obtained in 55% yield, dissolved in dry pentane and kept at −20° C. until used.

([a] triflic anhydride is trifluoromethanesulfonic anhydride)

3. (4S,2'R)-3-(2'-isopropyl-1'-oxopentyl)-4-benzyl-2-oxazolidinone

Under N$_2$ to a cooled (−78° C.) solution of dry diisopropylamine (11 ml) in dry THF (40 ml) was added dropwise n-BuLi (49 ml, 1.6 M solution in hexane). After stirring the reaction mixture for 30 min a cooled (−78° C.) solution of (4S)-3-(1'-oxopentyl)-4-benzyl-2-oxazolidinone (18.5 g in 70 ml dry THF) is slowly added via cannula. After stirring for 1 hour, a cooled (−78° C.) solution of isopropyl triflate (15 g in 40 ml dry THF) is added via cannula. The reaction slowly warmed to −20° C., left overnight at −20° C. and quenched by saturated NH$_4$Cl solution. Total reaction time was 20 hours. THF evaporated and the residue extracted with Et$_2$O (3×150 ml) and dried over MgSO$_4$. Purification of the crude product (23 g of a yellow oil) by column chromatography (silica gel, 0.5–3% EtOAc in PE) afforded 8.8 g of a yellowish oil, 41% yield.

4. (2R)-propylisopropyl Acetic Acid ((2R)-PIA)

To a cooled (0° C.) solution of (4S,2'R)-3-(2'-isopropyl-1'-oxopentyl)-4-benzyl-2-oxazolidinone (8.8 g) in a mixture of THF:DDW (4:1, 550 ml) was added H$_2$O$_2$ (30%, 19.3 ml) followed by a solution of LiOH (2.44 g in 50 ml DDW). After stirring for 3 hours the reaction mixture was warmed to room temperature (~23° C.) and left overnight. After 24 hours the reaction mixture was cooled to 0° C. quenched by sodium sulfite (21 g in 100 ml DDW) and stirred for an additional hour. THF evaporated and the basic aqueous phase (PH=11) extracted with DCM (3×100 ml). The chiral auxiliary, (4S)-benzyl-2-oxazolidinone was obtained after evaporation of the DCM and crystallization from 20% EtOAc in PE, 80% yield. The aqueous phase was then acidified with concentrated HCl (PH=2) and extracted with EtOAc (3×100 ml). The combined organic extracts washed with saturated brine, dried on MgSO$_4$, evaporated and afforded the product, a colorless oil (3.49 g), yield 83%.

5. (2R)-propylisopropyl Acetamide ((2R)-PID)

Under N$_2$ to a cooled (0° C.) solution of (2R)-PIA (3.3 g) dissolved in dry DCM (100 ml) and dry DMF (1.77 ml) was added dropwise a solution of oxalyl chloride (34.3 ml, 2.0 M solution in DCM). After stirring one hour the DCM and excess oxalyl chloride were evaporated by N$_2$ stream. In order to remove traces of oxalyl chloride the crude product was treated with dry DCM (2×20 ml) which was evaporated by N$_2$ stream. To the crude reaction mixture dissolved in cooled (0° C.) dry DCM (100 ml) was added NH$_4$OH (20 ml, 25% solution in water) and the reaction mixture stirred for an hour. The organic phase washed with water and half saturated brine, dried over MgSO$_4$, filtered and concentrated. The product was crystallized from 20% EtOAc in PE to afford 2.14 g, 65% yield.

Synthesis of (2S)-propylisopropyl Acetamide 1. (4R,5S)-3-(1'-oxopentyl)-4-methyl-5-phenyl-2-oxazolidinone (4R,5S)-3-(1'-oxopentyl)-4-methyl-5-phenyl-2-oxazolidinone was synthesized from (4R,5S)-4-methyl-5-phenyl-2-oxazolidinone and valeroyl chloride by the same procedure as (4S)-3-(1'-oxopentyl)-4-benzyl-2-oxazolidinone. The product (29.55 g) was obtained in 84% yield.

2. (4R,5S,2'S)-3-(2'-isopropyl-1'-oxopentyl)-4-methyl-5-phenyl-2-oxazolidinone (4R,5S,2'S)-3-(2'-isopropyl-1'-oxopentyl)-4-methyl-5-phenyl-2-oxazolidinone was synthesized from (4R,5S)-3-(1'-oxopentyl)-4-methyl-5-phenyl-2-oxazolidinone and isopropyl triflate by the same procedure as (4S,2'S)-3-(2'-isopropyl-1'-oxopentyl)-4-benzyl-2-oxazolidinone. The product (5.53 g) was obtained in 32% yield.

3. (2S)-propylisopropyl Acetic Acid ((2S)-PIA)

(2S)-PIA was synthesized from (4R,5S,2'S)-3-(2'-isopropyl-1'-oxopentyl)-4-methyl-5-phenyl-2-oxazolidinone by the same procedure as (2R)-PIA. The product (2.33 g) was obtained in 89% yield.

4. (2S)-propylisopropyl Acetamide ((2S)-PID)

(2S)-PID was synthesized from (2S)-PIA by the same procedure as (2R)-PID. The product (1.54 g) was obtained in 67% yield.

Pharmacokinetic Studies

Pharmacokinetic experiments were carried out on six mongrel dogs weighing 18–25 kg. Dogs were housed in an animal farm and were brought to the lab repeatedly every two-three weeks for crossover experiments after an overnight fast. Each dog was inserted with a urine (Levin's tube, Pennine Healthcare, Derby, UK) and two venous (20G/32 mm Venflon 2, Ohmeda, Helsingborg, Sweden) catheters located on different legs. Dogs were fed with commercial dog food four hours after drug injection, and had free access to water during the whole experiment.

Each dog was intravenously injected with 70 nmole/kg (10 mg/kg) of each enantiomer separately or 140 nmole/kg of the racemate, dissolved in 2 ml of 96% ethyl alcohol. Venous blood samples (6 ml) were withdrawn via an indwelling catheter from the other leg than used for injection, and transferred into heparinized tubes. The blood samples were centrifuged at 3000 g for 10 minutes, plasma was then separated and stored at 20° C. until analyzed. Blood collection commenced at 5 minutes, and continued up to 12 hours after injection. Urine samples were collected in 1–2 hour intervals beginning at 1 hour and up to 12 hours after injection. The urine volume was recorded and an aliquot was stored at 20° C. until analyzed.

Assay of plasma samples: to test tubes containing 2 $\mu$g of the internal standard (diisopropyl acetamide), 0.5 ml of plasma (thawed at room temperature) and 5 ml of tert-butyl methyl ether (TBME) was added. The test tubes were vigorously vortexed for 30 sec and centrifuged at 3000 g for 10 minutes. The organic phase was separated and dried under reduced pressure using a vortex evaporator. Samples were then reconstituted with 150 $\mu$l of chloroform and dried under reduced pressure without vortexing. The sample was again reconstituted with 30 $\mu$l of chloroform, of which 2 $\mu$l were injected into the GC apparatus.

The column used for the chromatographic analysis of PID enantiomers was a Mosandl-methyl capillary column (10 m, 0.25 mm, 0.25 µm) coated with: Heptakis (2,3-di-O-methyl-6-O-tert-butyldimethylsilyl)-β-cyclodextrin as the stationary phase and nitrogen as carrier gas (takeo carbohydr res). Column head pressure was set at 50 KPa, split ratio 1:30, oven temperature 120° C., injector temperature 250° C. and detector temperature 250° C. At these conditions S-PID had a retention time of 4.6 min, R-PID 5.1 min.

The results (FIGS. 4 and 5) show that when enantiomers are given individually, PID exhibits a clear stereospecific kinetics. But, when PID is given in a racemic mixture, no sterospecifity is observed and the parmacokinetic parameters are very close to those of the individual R enantiomer.

The Pharmacokinetic parameters of the individual enantiomers and of the racemic mixture are summarized in Table 1 and Table 2 respectively.
(CL=clearance, $V_\beta$=volume of distribution, Vss=$V_\beta$ at steady state, MRT=Mean Residence Time, E=liver extraction ratio, fe=fraction excreted unchanged in the urine)

TABLE 1

Pharmacokinetic Parameters of PID Enantiomers in Dogs given as individual enantiomers (10 mg/kg, via iv)

|  | (R)-PID | (S)-PID | S/R |
| --- | --- | --- | --- |
| CL (L/h) | 6.8 ± 1.6 | 11.3 ± 1.5 | 1.66* |
| $V_\beta$ (L) | 13.1 ± 2.2 | 17.0 ± 2.9 | 1.29 |
| Vss (L) | 16.0 ± 1.2 | 19.1 ± 2.7 | 1.19 |
| t½ (h) | 1.37 ± 0.2 | 1.04 ± 0.1 | 0.76* |
| MRT (h) | 2.57 ± 0.5 | 1.83 ± 0.3 | 0.71* |
| E (%) | 15.0 ± 4.6 | 23.7 ± 3.5 | 1.58* |
| fe (%) | 0.50 ± 0.4 | 0.40 ± 0.4 | 0.78* |

*$P < 0.05$.

TABLE 2

Pharmacokinetic Parameters of PID Enantiomers in Dogs given in a racemic mixture (20 mg/kg, via iv)

|  | (R)-PID | (S)-PID | S/R |
| --- | --- | --- | --- |
| CL (L/h) | 6.0 ± 1.7 | 6.0 ± 1.8 | 1.0 |
| $V_b$ (L) | 10.2 ± 0.9 | 10.4 ± 1.4 | 1.0 |
| Vss (L) | 15.7 ± 1.5 | 15.7 ± 0.9 | 1.0 |
| t½ (h) | 1.25 ± 0.3 | 1.27 ± 0.3 | 1.0 |
| MRT (h) | 2.83 ± 0.6 | 2.87 ± 0.7 | 1.0 |
| E (%) | 12.5 ± 4.0 | 12.1 ± 4.1 | 1.0 |
| fe (%) | 0.60 ± 0.45 | 0.66 ± 0.46 | 1.1 |

Epoxide Hydrolase Inhibition Assay

PID is known to be an inhibitor for Epoxide Hydrolase (EH) activity. A study was conducted in order to explore the possibility of PID stereospecificy in the EH inhibition. The study was conducted as follows:

The in vitro microsomal EH inhibitory potency of racemic PID and its individual enantiomers was measured in human liver microsomes with S-(+)-styrene oxide (SO) as substrate. Microsomes were prepared from human liver #135 (HL-135), genotypically classified as a wild type EH, according to the previously published procedure (Rattie (1989) Drug Metabolism and Disposition, 17: 265–270). The rate of S-(+)-1-phenyl-1,2-ethanediol (PED) formation was measured in microsomal incubations, as previously described, with slight modifications (Kerr (1989) Clinical Pharm. Therp. 46: 82–93). Briefly: Racemic PID, S-PID, R-PID or 0.1M sodium phosphate buffer PH 7.4 were preincubated with microsomal protein for 1.5 min at 37° C., before the reaction was started by addition of SO. The reaction was terminated by the addition of 3 ml n-hexane, rapid vortexing for 30 sec, and placing the tubes on ice until processed further. The background hydrolysis rate for SO was measured by replacement of microsomal protein with an equal amount of denatured microsomal protein. All reported PED formation rates have been corrected for the non-enzymatic hydrolysis. The final protein concentration was 5.34 µg/ml. SO was added in a 15 µl acetonitrile solution, such that the final SO concentration was 25 µM (equals the $K_m$ of SO). PID and its individual enantiomers were added in a 15 µl methanolic solution, such that the final concentration of organic solvent was 1%. The inhibition reactions were investigated at five concentrations ranging from 4 to 30 µM. Positive control for 50% inhibition was done by using 5 µM VPD (equals the $IC_{50}$ of VPD). All determinations were made in triplicates.

PED was extracted and assayed using a reverse phase HPLC procedure previously published, with slight modifications (Kerr, (1989) Clinical Pharm. Therp. 46: 82–93). Internal standard was felbamate 1.6 µg in 100 µl methanolic solution. Microsomal incubations were extracted with 7 ml TBME. Mobile phase composition: double distilled water/acetonitrile/methanol 70:20:10. Flow rate was set at 1.2 ml/min and the compounds detected by UV absorption at 210 nm. Chromatographic separation was carried out on a Zorbax $C_8$ column (5 µM, 4.6×25 cm) equipped with a $C_8$ guard column (5 µM, 4.6×1.0 cm).

The inhibition of EH mediated SO hydrolysis by PID and the individual enantiomers; S-PID and R-PID, was examined in microsomal suspensions that were prepared from a single human liver, HL-135. The PED formation rates are presented inn FIG. 6. From percent remaining activity of EH vs. inhibitor concentration plots, $IC_{50}$ values could be derived for each of the tested compounds. Racemic PID had an $IC_{50}$ of 8.55 µM, S-PID an $IC_{50}$ of 7.60 µM and R-PID an $IC_{50}$ of 11.20 µM.

Average non-enzymatic SO hydrolysis rates were 6.67±0.47% of the control enzymatic hydrolysis rates. VPD (5 µM) as a positive control inhibited SO hydrolysis by 51.5±2.4% of the control enzymatic hydrolysis rates. QC of four different PED concentrations within the PED concentration range had an accuracy of 0.55–2.70% and reproducibility (% CV) of 1.49–5.61%.

Biological Activity

1. Teratogenicity Study

1a. Teratogenicity (Finnel) Study in SWV Mice

Teratogenicity was evaluated in the highly inbred SWV mice strain on the basis of their known susceptibility to VPA-induced NTDs (Finnel et al. (1988) Teratology 38: 313–320). The mice were maintained on a 12 h light cycle in the Animal Resources Facility at The college of Veterinary Medicine, Texas A&M University. Mice were pathogen free and were allowed free access to Wayne TekLad rodent chow and tap water. Virgin females, 40–60 days of age were bred overnight and examined the next morning for the presence of vaginal plugs. The beginning of gestation (day 0) was set at 10 P.M. of the previous evening, the midpoint of the dark cycle (Finnel et al. (1988) Teratology 38: 313–320). Ten dams were randomly assigned to each of the tested compounds; racemic PID, S-PID and R-PID. At day 8.5 of gestation, each dam was exposed to a single intraperitoneal (ip) injection of the tested compound (500–600 mg/kg) or the vehicle (1% carboxymethyl cellulose—CMC). Following administration, the dams were returned to their cages until day 18.5 of gestation. At that time the dams were sacrificed by cervical dislocation, the abdomen opened and the uterine contents removed. The location of all-viable embryos or fetuses and resorption sites were recorded, and the embryos were examined for the presence of exencephaly.

Teratogenicity in the SWV mice strain was evaluated following a single ip administration of PID, S-PID and R-PID to ten dams at day 8.5 of gestation. Teratogenic data is presented in Table 1. Both PID and R-PID were administered at doses of 600 mg/kg. Due to several incidences of maternal lethality following 600 mg/kg administration of S-PID, teratogenicity was further investigated at 500 mg/kg. Both racemic and R-PID failed to induce exencephaly in the SWV embryos. S-PID caused 0.8% exencephaly, but this was not different from controls (0%). Resorption rates induced by PID, S-PID and R-PID were 6.3%, 6.1% and 10.4%, respectively, which is not different from controls, 8.6%.

Sodium valproate (VPA-Na), racemic PID, (2R)-PID and (2S)-PID were suspended in a 25% Cremophor EL aqueous solution. For another treatment group, VPA-Na was dissolved in distilled water. The pregnant dams were injected with a single 3 mmol/kg subcutaneously dose (10 ml/kg volume administered) on the morning of day 8 of gestation. Mice of the control group were injected with the vehicle, 25% Cremophor EL solution (10 ml/kg volume administered). On day 18 of gestation the dams were sacrificed by cervical dislocation, the uteri removed and the number of implantations, resorptions and dead fetuses recorded. Living fetuses were weighed individually and inspected for the presence of external malformations.

TABLE 3

Teratogenic effects of PID, R-PID and S-PID in SWV mice

| Compound | Dose (mg/kg) | Litters | Implants | Resorption | Live Fetuses | Exencephaly |
|---|---|---|---|---|---|---|
| Control[3] | 0 | 11 | 148 | 1 (0.7) | 147 | 0 |
| PID | 600 | 10 | 126 | 8 (6.3)* | 118 | 0 |
| R-PID | 600 | 10 | 134 | 14 (10.4) | 120 | 0 |
| S-PID | 500 | 10 | 131 | 8 (6.1)* | 123 | 1 (0.8) |

[1]Percent of total implants
[2]of live fetuses
[3]Controls were administered with the vehicle: CMC 1%
*Significantly different relative to controls ($P < 0.05$)

1b. Teratogenicity (Nau) Study in Mice of NMRI Strain

Mice of the NMRI strain (Harlan-Winkelmann GmbH, 33176 Borchen, Germany) were kept under controlled conditions: Room temperature ($21\pm1°$ C.), relative humidity ($50\pm5\%$), and a 12 hour light-dark cycle with the light period from 10 a.m. to 10 p.m. Females weighing 28 to 36 g were mated with males of the same strain for 3 hours (from 6 a.m. to 9 a.m.). Animals with vaginal plugs were separated, and the following 24 hour period was designated as day 0 of pregnancy. The animals were given free access to food (Altromin 1324 diet, Lage, Germany) and tap water. Approval for the study was obtained from the Department of Health.

Teratogenic potency of racemic PID and the individual enantiomers was evaluated in NMRI mice following a single 3 mmol/kg subcutaneous injection to pregnant dams at day 8 of gestation, as presented in Table 4. Racemic PID and the individual enantiomers failed to induce exencephaly in the developing mouse embryos, whereas VPA caused 37% and 73% exencephaly in living fetuses when administered in aqueous solution and Cremophor suspension, respectively. Fetal deaths and early resorptions expressed as embryolethality was significantly increased in VPA-treated animals, whereas all PID groups and controls had comparable rates. All treatment groups (PID and VPA) had significant reduction in fetal weight.

TABLE 4

Teratogenicity of racemic PID, (2R)-PID and (2S)-PID in NMRI mice at day 18 of gestation.

| Compound | Dose mmol/kg | Litters n | Total Implants n | Live Fetuses n | Fetal Weight[1] g | Embryo-lethality[2] n (%) | Exence-phaly[3] n (%) |
|---|---|---|---|---|---|---|---|
| (2R)-PID4 | 3 | 9 | 92 | 78 | 1.16 ± 0.08* | 14 (15.2) | 0 (0) |
| (2S)-PID4 | 3 | 5 | 64 | 58 | 1.15 ± 0.09* | 6 (9.4) | 0 (0) |
| Racemic PID4 | 3 | 8 | 96 | 87 | 1.21 ± 0.07 | 9 (9.4) | 0 (0) |
| VPA-Na4 | 3 | 7 | 86 | 41 | 0.96 ± 0.08* | 45 (52.3)** | 30 (73.2)** |
| VPA-Na5 | 3 | 8 | 92 | 63 | 1.09 ± 0.11* | 29 (31.5)** | 23 (36.5)** |
| Controls | — | 20 | 258 | 238 | 1.23 ± 0.09 | 20 (7.8) | 3 (1.3) |

[2]Percent of total implants
[3]Percent of live fetuses
[4]Administered subcutaneously in the vehicle: 25% Cremophor EL.
[5]Administered intraperitonealy dissolved in distilled water.
[6]Controls received the vehicle: 25% Cremophor EL.
*Significantly different from controls ($p < 0.0001$, Fisher's Exact test)
**Significantly different from controls ($p < 0.0001$, Student's t-test)

2. Anti-migraine Activity of PID.

The GABA transaminase inhibitor and activator, of glutamic acid, the decarboxylase, valproic acid is being used for the treatment of migraine. In this study, a valproyl amide analog (PID) in a racemic form, was tested in animal models (rats) for the treatments of migraine and pain, in comparison to VPA.

The animal model used in this study is the one developed by Moskowitz et al. (F. M. Cutrer, V. Limmroth and M. A. Moskowitz: Possible mechanisms of valproate in migraine prophylaxis, *Cephalalgia* 17:93–100 (1997)). Moskowitz et. al. examined the plasma protein extravasation following electrical trigeminal ganglion stimulation or intravenous administration of substance P. It was concluded that in this model valproic acid blocks plasma extravasation in the meninges through $GABA_A$-mediated postjunctional receptors probably within the meninges. The dosages required are comparable to those used clinically. Thus, agonists and modulators at the $GABA_A$ receptor may become useful for the development of selective drugs for migraine and cluster headache (W. S. Lee et. al.: Peripheral GABAA receptor mediated effects of sodium valproate on durnal plasma protein extravasation to substance P and trigeminal stimulation, *Toward Migraine* 2000, F. C. Rose Ed. Elsevier, Amsterdam, 1996, pp.289–319).

Figure 7A:
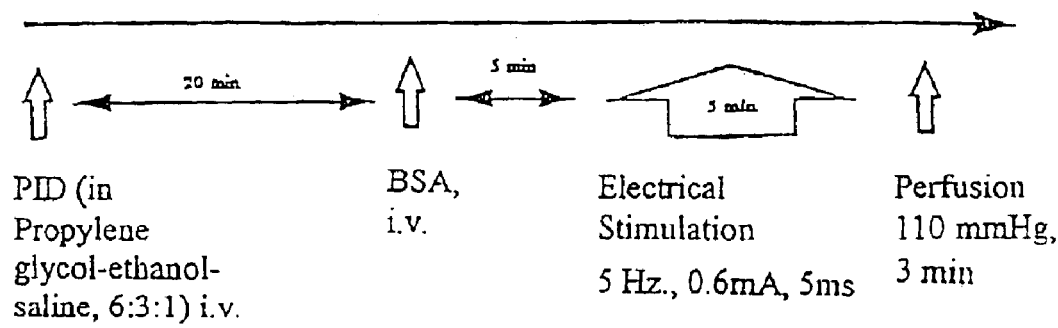
Figure 7B:
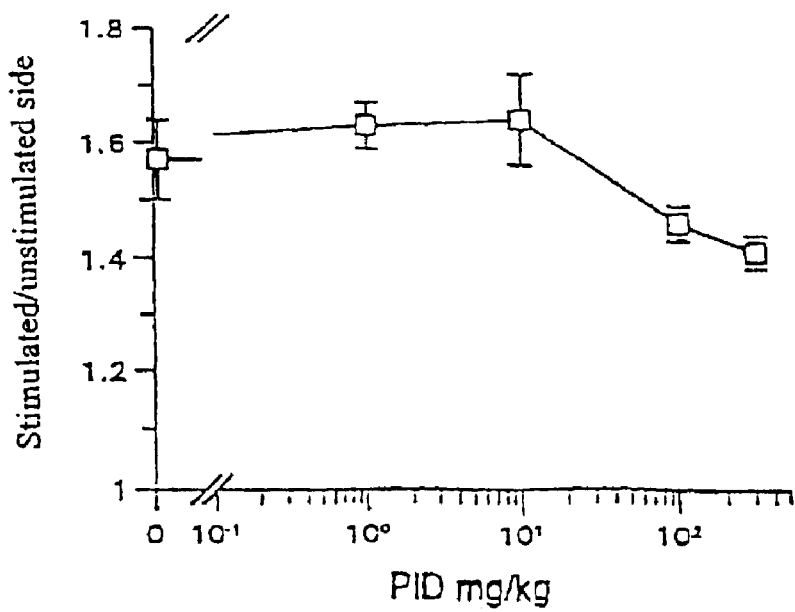

We tested the effects of PID on dural plasma protein (Bovine Serum Albumine—BSA) extravasation evoked by unilateral trigeminal gangelion stimulation in anaesthetized rats. The results of this study, shown in FIG. 7, show that PID has inhibitory effects on the dural plasma protein extravasation, i.e., it has the potency for anti-migraine and anti-pain activity.

3. Anticonvulsant Activity and Neurotoxicity of PID in Mice

Individual enantiomers of PID were screened in mice for their anticonvulsant activity (by the NIH Epilepsy Branch) following intraperitoneal administration to mice by employing a screening procedure which involves: (i) the maximal electoshock (MES) test, which measures seizure spread; (ii) the subcutaneous pentylenetetrazol test sc. Met. Test), which measures seizure threshold; and (iii) the rotorod ataxia test, which assesses neurotoxicity.

Table 6 shows the results obtained in this study:

TABLE 6

Anticonvulsant Activity and Neurotoxicity of PID in Mice (intraperitoneal administration)

|  | PID | (S)-PID | (R)-PID | S/R |
|---|---|---|---|---|
| MES | 122 | 145 | 110 | 1.32 |
| sc Met | 77 | 80 | 67 | 1.19 |
| Neurotox. | <120 | 118 | <145 | >0.81 |
| PI-MES | <0.98 | 0.81 | <1.3 |  |
| PI-sc Met | <1.56 | 1.46 | <2.2 |  |

4. Anticonvulsant Activity and Neurotoxicity of PID in Rats

Individual enantiomers of PID were screened in rats for their anticonvulsant activity following oral feeding, by the procedure described in the previous section. The $ED_{50}$ values obtained in this study are as follows:

$ED_{50}$ for (2R)-PID: 16 mg/kg $ED_{50}$ for (2S)-PID: 26 mg/kg $ED_{50}$ for racemate: 22 mg/kg.

What is claimed is:

1. Substantially pure (R)-propylisopropyl acetamide.

2. Substantially pure (S)-propylisopropyl acetamide.

3. A pharmaceutical composition comprising substantially pure (R)-propylisopropyl acetamide and at least one pharmaceutically acceptable excipient.

4. A pharmaceutical composition comprising substantially pure (S)-propylisopropyl acetamide and at least one pharmaceutically acceptable excipient.

5. A method for treating a medical condition selected from the group consisting of neurological disorders, psychotic disorders, affective disorders, pain, headaches, and migraines in a mammal in need of such treatment, said method comprising administering a therapeutically effective amount of a compound of claim 1 to said mammal.

6. A method for treating a medical condition selected from the group consisting of neurological disorders, psychotic disorders, affective disorders, pain, headaches, and migraines in a mammal in need of such treatment, said method comprising administering a therapeutically effective amount of a compound of claim 2 to said mammal.

7. A method for treating a medical condition selected from the group consisting of neurological disorders, psychotic disorders, affective disorders, pain, headaches, and migraines in a mammal in need of such treatment, the method comprising administering to said mammal a composition of claim 3 in an amount sufficient to provide therapeutically effective dose of (R)-propylisopropyl acetamide.

8. A method for treating a medical condition selected from the group consisting of neurological disorders, psychotic disorders, affective disorders, pain, headaches, and migraines in a mammal in need of such treatment, said method comprising administering to said mammal a composition of claim 4 in an amount sufficient to provide therapeutically effective dose of (S)-propylisopropyl acetamide.

* * * * *